United States Patent [19]

Broquet et al.

[11] Patent Number: 4,921,865

[45] Date of Patent: May 1, 1990

[54] AMINOACYLATES OF GLYCEROL ACETAL

[75] Inventors: Colette Broquet, Boulogne; Pierre Braquet, Garches, both of France

[73] Assignee: Societe de Conseils de Recherches et d'Applications Scientifiques (S.C.R.A.S.), France

[21] Appl. No.: 203,733

[22] Filed: Jun. 7, 1988

[30] Foreign Application Priority Data

Jun. 12, 1987 [GB] United Kingdom ................ 8713745

[51] Int. Cl.$^5$ .................... C07D 216/16; C07D 407/12
[52] U.S. Cl. ...................................... 514/336; 514/365; 514/307; 514/314; 514/385; 514/255; 546/283
[58] Field of Search ........................... 71/88; 548/336; 540/201, 481, 215; 546/283; 514/336

[56] References Cited

U.S. PATENT DOCUMENTS 4,035,178  7/1977  Konz ....................................... 71/88
4,375,474  3/1983  Walker ................................ 548/336

OTHER PUBLICATIONS

Morrison & Boyd, Organic Chemistry 4th Ed., 1983, p. 1282.

Primary Examiner—William R. Dixon, Jr.
Assistant Examiner—Miriam Sohn
Attorney, Agent, or Firm—Lucas & Just

[57] ABSTRACT

The invention relates to new aminoacylates of glycerol acetal of the general formula I

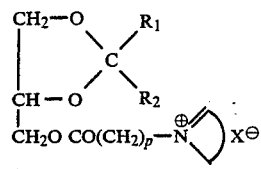

wherein
$R_1$ represents a substituted phenyl group or a group of the formula $C_mH_{2m+1}$, m being an integer of from 9 to 25,
$R_2$ represents a hydrogen atom, a phenyl group or a group of the formula $C_nH_{2n+1}$, n being an integer of from 1 to 10,
p is a integer of from 3 to 10,

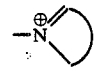

represents a nitrogen containing heterocyclic group and
$X^\ominus$ means a pharmaceutically acceptable anion to a preparation process of said compounds and to therapeutic compositions of matter containing the same.

6 Claims, 2 Drawing Sheets

AMINOACYLATES OF GLYCEROL ACETAL

The invention relates to aminoacylates of glycerol acetal, to a process for their preparation and to therapeutic compositions containing them.

The invention provides aminoacylates of glycerol acetal of the general formula I $$\begin{array}{l} CH_2-O \\ | \phantom{CH_2-}\diagdown \\ \phantom{CH_2-O}C \\ | \phantom{CH_2-}\diagup \phantom{aa} \diagdown R_2 \\ CH-O \\ | \\ CH_2O\ CO(CH_2)_p-\overset{\oplus}{N}\diagup\!\!\diagdown\ X^{\ominus} \end{array} \quad \text{I}$$

wherein

R$_1$ represents a substituted phenyl group or a group of the formula C$_m$H$_{2m+1}$, m being an integer of from 9 to 25, R$_2$ represents a hydrogen atom, a phenyl group or a group of the formula C$_n$H$_{2n+1}$, n being an integer of from 1 to 10, p is an integer of from 3 to 10, $$-\overset{\oplus}{N}\diagup\!\!\diagdown$$

represents a nitrogen containing heterocyclic group such as pyridinium, 3-thiazolinium, quinolinium, isoquinolinium, imidazolium and pyrazinium, and X$^{\ominus}$ means the anion of a pharmaceutically acceptable inorganic or organic acid, halogen ion such as chlorine, bromine, iodine or anions of benzoic acid, acetic acid, methanesulfonic acid, tartaric acid.

The compounds of the invention are interesting as anti-PAF agents (PAF means Platelets Activating Factor), with corresponding activity as anti-anaphylactic, antithrombotic, anti-platelet aggregant, anti-broncho constrictor, normo-tensive and anti-ischemic agents, immunodepressors, and active also against immune alteration of kidney, against various shocks, against skin allergies and intestinal ulcers induced by endotoxine for instance.

The invention further provides a process for the preparation of the compounds I as above defined, the process comprising reacting a slight stoichiometric excess of an aldehyde or ketone of the formula R$_1$COR$_2$, wherein R$_1$ and R$_2$ are as above defined, with glycerol in a non polar solvent, in the presence of p-toluenesulfonic acid and in refluxing conditions, reacting, at room temperature, the resultant 4-hydroxymethyl 1,3-dioxolan derivative with an ω-haloalkanoyl chloride of the formula ClCO(CH$_2$)$_p$X, wherein p and X are as above defined, in the presence of an organic base such as triethylamine, and reacting, at 50°–80° C. under nitrogen circulation, the resultant compound of the formula $$\begin{bmatrix} & O \diagdown \phantom{a} \diagup R_1 \\ & \phantom{aa} X \\ & O \diagup \phantom{a} \diagdown R_2 \\ \\ -OCO(CH_2)_p-X \end{bmatrix}$$

with a nitrogen containing heterocyclic compound of the formula $$\overset{\diagup\!\!\diagup}{N}\diagdown$$

They were obtained as a non-separated mixture of diastereoisomers, but may be separated by the usual methods.

This process is illustrated by the following reaction scheme.

steps $$R_1-\underset{\underset{O}{\|}}{C}-R_2 + CH_2OH-CHOH-CH_2OH \longrightarrow \quad a$$

$$\begin{bmatrix} & O \diagdown \phantom{a} \diagup R_1 \\ & \phantom{aa} X \\ & O \diagup \phantom{a} \diagdown R_2 \\ \\ -OH \end{bmatrix} \quad +$$

2

$$ClCO(CH_2)_pX \xrightarrow[CHCl_3]{NEt_3} \begin{bmatrix} & O \diagdown \phantom{a} \diagup R_1 \\ & \phantom{aa} X \\ & O \diagup \phantom{a} \diagdown R_2 \\ \\ -OCO(CH_2)_pX \end{bmatrix} \quad + \quad b$$

3

$$N\diagup\!\!\diagdown \longrightarrow \begin{bmatrix} & O \diagdown \phantom{a} \diagup R_1 \\ & \phantom{aa} X \\ & O \diagup \phantom{a} \diagdown R_2 \\ \\ -OCO(CH_2)_p-\overset{\oplus}{N}\diagup\!\!\diagdown \end{bmatrix} X^{\ominus} \quad \text{I} \quad c$$

The invention also provides a pharmaceutical composition comprising a compound of the general formula I as above defined in admixture with a pharmaceutically acceptable diluent or carrier.

The invention is illustrated by the following examples. Example 1 is set out in full; in the subsequent examples, only the characteristics of the substituents and of the resulting compounds are given (Unless otherwise specified, TLC is performed on silica gel plates).

EXAMPLE 1

2-heptadecyl 2-methyl 4-[4'-(N-pyridinium) butyryloxy methyl]-1,3-dioxolan chloride $-\overset{\oplus}{N}\bigcirc$ = pyridinyl,

Step a: Preparation of 2-heptadecyl 2-methyl 4-hydroxymethyl 1,3-dioxolan. a In an appropriate reactor were poured 11.1 g (40 mmol) of 2-nonadecanone, 6 g—which represents an excess with regard to the stoichiometric proportions—of twice distilled glycerol and 0.6 g of p-toluenesulphonic acid dissolved in 120 ml of dry toluene. The reaction mixture was refluxed under stirring for 12 hours and the resulting water was eliminated using a Dean Stark apparatus. After cooling, the organic phase was washed with 30 ml of 5% by weight aqueous solution of potassium hydroxide and then three times with the minimum amount of water. After drying over anhydrous sodium sulphate, the solvent was removed under reduced pressure. The residue was then purified by chromatography on a silica gel column. There were successively eluted the fraction of the ketone not involved in the reaction (petroleum ether : diethyl ether, 95:5 by volume), and then the dioxolan a (petroleum ether/diethyl ether 85:15 by volume). the dioxolan is a viscous product, partially crystallized.

Yield 11 g (78%).

rf: 0.18 (petroleum ether/diethyl ether 70:30 by volume).

IR 3500 cm$^{-1}$ (OH), 1100–1060 cm$^{-1}$ (C—O—).

Step b: 2-heptadecyl 2-methyl 4-(4'-chlorobutylryloxymethyl) 1,3-dioxolan. b A mixture of 6.4 g (18 mmol) of 2-heptadecyl 2-methyl 4-hydroxymethyl 1,3-dioxolan, prepared as described in step (a) above, and 6 ml (45 mmol) of triethylamine in 15 ml of dry chloroform was added dropwise to a solution of 6.25 g (22 mmol) of 4-chlorobutyryl chloride in 10 ml of dry chloroform at 0° C. The mixture was stirred for 12 hours at room temperature. After addition of 20 ml of chloroform, the mixture was washed with 1N aqueous solution of sodium hydroxide and then with water until the pH was 7. The elimination of the solvent left a residue which was chromatographed on a silica gel column with petroleum ether: diethyl ether as eluent, successively 95:5, then 90:10 and finally 80:20, by volume. There was thus obtained 7.6 g (yield 82 %) of an oily product which crystallized; melting point 39°–40° C. This product is a mixture of the two cis and trans isomers (separation of the same is uneasy).

rf: 0.45 and 0.37 (petroleum ether/diethyl ether 80:20 by volume).

IR 1740 cm$^{-1}$ (C=O), 1180–1160 cm$^{-1}$ (C—O—C ether and ester).

NMR 60 MHz, CDCl$_3$, (TMS.)

δ: 0.9 (triplet, 3H, CH$_3$ of the chain), 1.3 (mult., 35H, 32H+CH$_3$), 2.1 (mult., 2H, CO—CH$_2$—CH$_2$), 2.5 (triplet, 2H, CO—CH$_2$), 3.6 (mult., 4H, $\overline{CH_2}$—O and CH$_2$Cl), 4.2 (mult., 3H, CH$_2$OCO and CH—O).

Step c: 2-heptadecyl 2-methyl 4-[4'-(N pyridinium)-butyryloxymethyl]1,3-dioxolan chloride. I 5 g of the compound obtained in the previous step (b) above, dissolved in 30 ml of pyridine, was stirred at 80° C., under nitrogen for 24 hours. Excess pyridine was then eliminated under reduced pressure and the residue was purified by chromatography on silica gel. Elution with chloroform (for the recovery of starting material not involved in the reaction) and then with chloroform/methanol, first 90:10, then 80:20 by volume gave 3.80 g of the title product. This product is a mixture of the two cis and trans isomers (separation of the same is uneasy), yield 40% overall (65% for this step). Melting point 84°–85° C.

rf: 0.28 (CHCl$_3$/MeOH 70:30, by volume).

IR (nujol) 1740 cm$^{-1}$, 1630 cm$^{-1}$ (pyridine), 1200, 1180 cm$^{-1}$ (C—O—C).

NMR, 250 MHz, CDCl$_3$.

δ: 0.9 (triplet, 3H, CH$_3$), 1.2 (sing. large 3OH).

1.4 (doublet, 3H, $\overset{-O}{\underset{-O}{\diagdown\!\!\!\diagup}}\overset{}{CH_3}$) (the 2 CH$_3$ of the two diastereoisomers)

1.55 (mult., 2H, $\overset{-O}{\underset{-O}{\diagdown\!\!\!\diagup}}\overset{CH_2-}{}$ )

2.35 (mult., 2H, CO CH$_2$—CH$_2$), 2.6 (triplet, 2H, CO CH$_2$), 3.9 (mult., 1H, CH—O), 4 (mult., 2H, CH$_2$O CO), 4.2–3.6 (2 mult., 2H, CH$_2$O) (of the two diastereoisomers), 5.10 (mult., 2H, CH$_2$N$^{\oplus}$).

| pyridinium | { | 8 (mult., 2H, H$_\beta$) 8.4 (mult., 1H, H$_\gamma$) 9.6 (doub., 2H$_\alpha$) |
|---|---|---|

Mass spectrum:

M-Cl m/z: 504

$\bigcirc\overset{\oplus}{N}-(CH_2)_3-CO_2H$: 166

EXAMPLE 2

2-heptadecyl 2-methyl 4-[4'(N-quinolinium) butyryl oxymethyl]1,3-dioxolan chloride.

Step c: 5 g of the compound obtained in example 1 (step b) was dissolved in a mixture of 20 ml of quinolin and 20 ml of DMSO and heated at 80° C. under nitrogen for 4 days. Quinolin and DMSO were distilled under reduced pressure and the residue was chromatographed on a silica gel column. (eluent successively CHCl$_3$, then CHCl$_3$/MeOH 95:5). 2.5 g of the desired product were obtained as a mixture of the two diastereoisomers.

rf: 0.58 (CHCl$_3$/MeOH, 70:30).

IR ν quinolin 1650, 1630 and 1600 cm$^{-1}$.

Mass spectrum:

M-Cl m/z: 554

-continued

NMR quinolinium instead of pyridinium.

δ ppm: 7.90–8.10 (4H), 8.70 (1H), 8.90 (1H), 10.90 (1H$_\alpha$).

EXAMPLE 3

2-heptadecyl 2-methyl 4-[4'-(N-thiazolinium) butyryl oxymethyl]1,3-dixolan chloride.

Step c: 850 mg of the product obtained in example 1 (step b) in a mixture of thiazole (4 ml) and DMSO (6 ml) were heated at 80° C. for 24 hours. The reaction mixture was evaporated in vacuo and the residue was chromatographed on a silica gel column, eluent CHCl$_3$/MeOH 50:50 giving a viscous product.

rf: 0.34 (CHCl$_3$/MeOH 70:30).

NMR thiazolinium instead of pyridinium.

δ ppm: 8.19 (d: 1H), 8.4 (d: 1H), 10.90 (sing. 1H).

Mass spectrum: M - Cl: 510 m/z.

EXAMPLE 4

2-heptadecyl 4-[4'-(N-pyridinium) butyryloxymethyl] 1,3-dioxolan chloride.

$R_1 = C_{17}H_{35}$, $R_2 = H$,

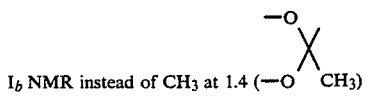

I$_b$ NMR instead of CH$_3$ at 1.4 (—O   CH$_3$)

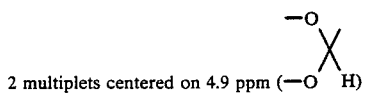

2 multiplets centered on 4.9 ppm (—O   H)

X=Cl, p=3.

2 b rf: 0.17 (petroleum ether/diethyl ether 30:70 by volume).

3 b rf: 0.37 (petroleum ether / diethyl ether 70:30 by volume).

I$_b$ rf: 0.16 (chloroform / methanol 70:30 by volume).

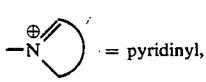

Mass spectrum: M - Cl: 490 m/z.

EXAMPLE 5

2-heptadecyl 4[4'-(N-quinolinium) butyryl oxy methyl] 1,3 dioxalan chloride.

$R_1 = C_{17}H_{35}$, $R_2 = H$,

X=Cl, p=3.

rf: 0.48 (chloroform/methanol 70:30 by volume.)

EXAMPLE 6

2-heptadecyl 2-(n-propyl 4-(4'-(N-pyridinium) butyryl oxy methyl]1,3-dioxolan chloride.

$R_1 = C_{17}H_{35}$, $R_2 = $ n-propyl,

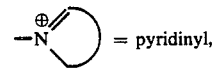

X=Cl, p=3.

2c rf: 0.23 (petroleum ether/diethyl ether 70:30 by volume).

3c rf: 0.38 (petroleum ether/diethyl ether 80:20 by volume).

I$_c$ rf: 0.20 (chloroform/methanol 70:30 by volume).

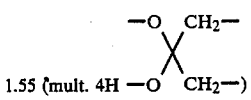

1.55 (mult. 4H —O   CH$_2$—)

1.2 (32H)

0.9 (triplet, 6H, 2CH$_3$)

Mass spectrum: M - Cl: 532 m/z.

EXAMPLE 7

2-heptadecyl 2-methyl 4-[5'-(N-pyridinium) pentanoyl oxymethyl]1,3-dioxolan chloride.

$R_1 = C_{17}H_{35}$, $R_2 = CH_3$,

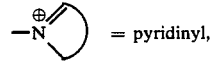

X=Cl, p=4.

rf: 0.23 (chloroform/methanol 70:30).

EXAMPLE 8

2-(3,4,5-trimethoxy phenyl) 2-methyl 4-[4'-(N-pyridinium)butyryloxymethyl] 1,3-dioxolan chloride.

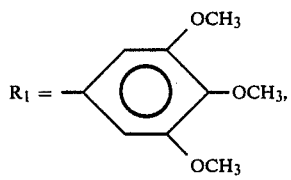

$R_2 = CH_3$,

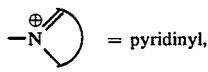 = pyridinyl,

X=Cl, p=3.
2d rf: 0.32 (chloroform/methanol 98:2 by volume).
3d rf: 0.61 (chloroform/methanol 98:2 by volume).
$I_d$ rf: 0.34 (chloroform/methanol 60:40 by volume).
IR 1735 (C=O), 1610 (pyridine), 1590 (benzene), 2740 (OCH₃).
$I_d$ NMR instead of the chain $R_1$ 1.5 ppm (m, 3H, —O–C(—O)–CH₃) for $R_2$ 3.7 (sing., 9H, OCH₃)

6.8 (2H arom.)

Mass spectrum: M - Cl: 432 m/z.

EXAMPLE 9

2-heptadecyl 2-methyl 4-[6'-(N-pyridinium) hexanoyloxymethyl] 1,3 dioxolan bromide.

$R_1 = C_{17}H_{35}$, $R_2 = CH_3$,

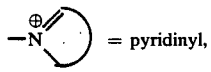 = pyridinyl,

X=Br, p=5.

step b: 2-heptadecyl 2-methyl 4-(6'-bromo hexanoyloxymethyl) 1,3-dioxolan bromide.

Following the procedure described in example 1, using 6-bromo-hexanoyl chloride, the desired product was obtained as a viscous product (yield 82 %).
rf: 0.57 (petroleum ether/ether 80:20).

step c: Following the procedure described in example 1, the desired product was obtained as a viscous product (yield 70 %).

rf 0.36 (CHCl₃ / MeOH 70:30).
IR 3450 cm⁻¹ (residual water).
$\nu$CO $^{1740}$, $\nu$C—O—C $^{1180}$, $\nu$pyridine $^{1640}$ cm⁻¹.
NMR 500 MHz CDCl₃, δ (TMS) 0.85 (triplet, 3H, CH₃); 1.25 (sing. large 30H);

1.35 (d, 3H, —O–C(—O)–CH₃, Z + E);

1.45 (mult., 2H, CH₂δ); 2.1 (mult., 2H, COCH₂CH₂); 2.35 (mult., 2H, COCH₂); 3.70 and 4.35 (mult., 2H, CH₂O, Z+E); 4(mult. 3H, CH₂OCO and H—C—O); 5.05 (triplet, 2H, CH₂N⊕).
pyridinium 8.1 (triplet, 2H, H$_\beta$); 8.6 (triplet, 1H, H$_\gamma$); 9.5 (d: 2H, H$_\alpha$).
U. V. (Ethanol) logε 3.65 λ 258.8 nm.
Mass spectrum :

M-Br m/z: 532

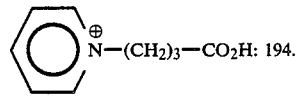: 194.

EXAMPLE 10

2-heptadecyl 2-methyl 4-[6'-(N-quinolinium) hexanoyloxymethyl) 1,3-dioxolan bromide.

rf : 0.60 (CHCl₃/MeOH 70:30).
IR Quinolinium 1650, 1630, 1600 cm⁻¹.
U. V. (Ethanol) logε 4.53 λ 235.4 nm, 2.18 λ 316.5 nm.
NMR quinolinium instead of pyridinium.
δ: 5.5 (2H, CH₂N⊕), 7.90–8.40 (5H), 9.10 (1H), 10.70 (1H, Hα).
Mass spectrum:

M-Br m/z: 582

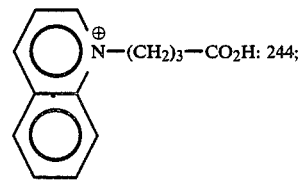: 244;

EXAMPLE 11

2-heptadecyl 2-methyl 4-[6'-(N-isoquinolinium) hexanoyloxymethyl) 1,3-dioxolan bromide.

step c: Using isoquinoline instead of quinoline.
rf: 0.55 (CHCl₃ / MeOH 73:30).
IR isoquinolin 1650, 1610, 1590 cm⁻¹.
NMR isoquinolinium instead of quinolinium.
δ: 5.15 (triplet, 2H, CH₂N⊕); 7.95–8.40 (4H); 8.80 (2H); 11.05 (1H).
Mass spectrum: M - Br: 582 m/z.

EXAMPLE 12

2-heptadecyl 2-methyl 4-[11'-(N-pyridinium undecanoyloxymethyl) 1,3-dioxolan bromide.

$R_1 = C_{17}H_{35}$, $R_2 = CH_3$,

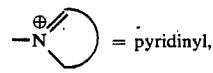 = pyridinyl,

X=Br, p=10.

step b: 2-heptadecyl 2-methyl 4-(11'-bromo undecanoyloxymethyl) 1,3-dioxolan.

Following the procedure described in example 1, using 11-bromo undecanoyl chloride, the desired product was obtained.
Melting point: 52° C. (yield 60%),.
rf: 0.26 (petroleum ether/ether 85:15).

step c

Melting point: 92° C.
rf 0.45 (CHCl₃/MeOH 70:30).
Mass spectrum: M - Br: 602 m/z.

EXAMPLE 13

2-heptadecyl 2-(n-propyl) 4-[6'-(N-pyridinium) hexanoylmethyl] 1,3-dioxolan bromide.

$R_1 = C_{17}H_{35}$, $R_2 = $ n-propyl,

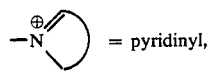 = pyridinyl,

X = Br, p = 5.
rf: 0.44 (CHCl$_3$/MeOH 70:30).
Melting point: 76° C.
Mass spectrum: M - Br : 560 m/z.

EXAMPLE 14

2-nonyl 2-methyl 4-[6'-(N-pyridinium hexanoyloxymethyl] 1,3-dioxolan bromide.

$R_1 = C_9H_{19}$, $R_2 = CH_3$,

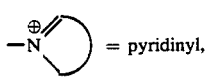 = pyridinyl,

X = Br, p = 5.

step b
rf: 0.50 (petroleum ether/ether 80:20).

step c
rf: 0.30 (CHCl$_3$/MEOH 70:30).
Mass spectrum: M - Br: 420 m/z.

TOXICOLOGY

The compounds of the invention have been administered to mice for determination of acute LD$_{50}$. For all the compounds of the invention LD$_{50}$ was over 300 mg/Kg (IP or SC) and 600 mg/Kg (PO).

PHARMACOLOGY

A proof of the pharmaceutical interest of the compounds of the invention has been established by the following pharmaceutical experimentations :

1—INHIBITION OF THE PLATELETS AGGREGATION ON NEW ZEALAND RABBITS

The experimentation was conducted on platelets with plasma of New Zealand rabbits.

Blood samples were taken from auricular artery and placed in a citrate buffer (3.8 % ; pH 7.4) ; blood was further centrifugated for 15 mn at 1200 RPM.

The tested sample was prepared in DMSO, then poured on platelets rich plasma for 1 mn, then a dose of 2.5 nM of PAF was added.

The determination is made on a Cronolog Coultronics apparatus which determines the transmission percentage corresponding to the maximum height of the peak before the desaggregation.

The percentage of variation of the inhibition with respect to the transmission percentage is calculated (control: pure DMSO).

This method was described in details in LABORATORY INVESTIGATIONS, Vol. 41, No. 3, p. 275, 1979, JEAN-PIERRE CAZENAVE, Dr. MED. , JACQUES BENVENISTE, Dr. MED., AND J. FRASER MUSTARD, M.D., "Aggregation of Rabbits Platelets by Platelet-Activating Factor Is Independent of the Release Reaction and the Arachidonate Pathway and Inhibited by Membrane-Active Drugs".

The results demonstrate that the compounds inhibit the aggregation induced by 2.5 nM of PAF. Five tests made on 5 different rabbits allowed us to calculate the IC$_{50}$ of the various compounds using the linear regression test.

| Inhibition of PAF induced platelet aggregation in platelet rich plasma from rabbits. | |
|---|---|
| Example No. | IC$_{50}$ PRP (M) |
| No. 1 | $2.2 \cdot 10^{-6}$ |
| No. 2 | $1.2 \cdot 10^{-6}$ |
| No. 3 | $2.15 \cdot 10^{-5}$ |
| No. 4 | $7 \cdot 10^{-6}$ |
| No. 5 | $3.1 \cdot 10^{-6}$ |
| No. 6 | $3.04 \cdot 10^{-6}$ |
| No. 7 | $5 \cdot 10^{-6}$ |
| No. 8 | $1.13 \cdot 10^{-5}$ |
| No. 9 | $4.04 \cdot 10^{-7}$ |
| No. 10 | $3.03 \cdot 10^{-7}$ |
| No. 12 | $3.12 \cdot 10^{-5}$ |
| No. 13 | $1.73 \cdot 10^{-6}$ |
| No. 14 | $1.46 \cdot 10^{-6}$ |

2—BINDING

MATERIAL AND METHOD

Synthetic tritiated [$^3$H]-PAF used was in ethanol solution with a specific activity of 59.5 ci/mmols. Unlabelled PAF and lyso-PAF were solubilized in ethanol solution and stored at −80° C. The compounds were solubilized in DMSO.

Platelet membrane preparation

Rabbit whole blood (6 volumes) was drawn from the central ear artery into 1 volume of ACD solution (citric acide 1.4 g, sodium citrate 2 5 g, Dextrose 2 g per 100 ml of H$_2$O) and centrifuged at 150 g for 15 minutes. The platelet-rich plasma (PRP) was carefully removed and centrifuged for 15 minutes at 1000 g. The platelet pellet was then washed 3 times: twice in Tris-HCl buffer 10 mM, pH 7.4 containing NaCl 150 mM, MgCl$_2$ 5 mM, EDTA 2 mM and the last time in the same but sodium-free buffer.

The platelet pellet was resuspended in this latter buffer, quickly frozen in liquid nitrogen and slowly thawed at room temperature for at least 3 times as described by T. Y. Shen et al. The lysed platelets were centrifuged at 100,000 g for 30 minutes in a BECKMAN model L8.55 ultra centrifuge (rotor 50.2 Ti). Platelet membrane homogenate was stored at −80° C. and used within two weeks without noticeable changes in PAF-acether binding characteristics.

Protein contain was determined by the Lowry method using bovine serum albumine as standard.

Binding assay 60 to 100 μg of membrane proteins were added to a final volume of 1 ml in plastic tubes containing 1 nM [$^3$H]-PAF in Tris-HCl 10 mM pH 7 buffer containing 0.025 % bovine serum albumin and incubated with or without unlabelled PAF or PAF-antagonists. The incubation was carried out for 1 h 30 at 0° C. The bound [$^3$H]-PAF was separated from the free [$^3$H]-PAF by immediate filtration through whatman GF/C glass fiber filters under vacuum (Brandel system). The reaction and the filters were washed 3 times with 5 ml of ice-cold buffer. The filters were then placed into polyethylene phials filled up with 10 ml of liquid scintillation fluid and the radioactivity was measured by an LKB $\beta$ counter with 45% efficiency.

The non specific binding was determined in the presence of $10^{-6}$M of unlabelled PAF. The specific binding was calculated by substracting non specific binding from the total binding. The inhibition by compounds on the specific [$^3$H]-PAF binding was determined as the percent inhibition by the equation:

$$\% \text{ inhibition} = \frac{(^3\text{H-PAF total bound}) - \left(\begin{array}{c} ^3\text{H-PAF bound in presence} \\ \text{of compounds} \end{array}\right)}{^3\text{H-PAF specifically bound}} \times 100$$

| Example No. | IC$_{50}$ |
|---|---|
| No. 1 | $4.5 \cdot 10^{-7}$ |
| No. 9 | $3.5 \cdot 10^{-8}$ |
| No. 10 | $3.5 \cdot 10^{-8}$ |
| No. 14 | $6.1 \cdot 10^{-7}$ |

3—BRONCHOCONSTRICTION, LEUKOPENIA AND THROMBOCYTOPENIA INDUCED BY PAF IN THE GUINEA PIG

MATERIALS AND METHODS

Male Guinea-pig (400–500 g) were anesthetized with urethane (1.5 g/kg: IP) prior to be tracheotomized and ventilated with a respiratory pump (UGO BASILE) (70–80 breath/minute, 1 ml air/100 g/breath) to abolish spontaneous respiration a pneumothorax was performed. The resistance to inflation was measured with a pressure transducer (UGO BASILE) against an initial pressure of 10 cm H$_2$O according to Konzett and Rossler. Animals were allocated into groups and were treated or not by the compounds of the invention (0.05, 0.1, 0.5, 1 and 5 mg/kg). The products were given IV 1 hour before challenge with PAF.

The animals were challenged with various doses of PAF (30–100 n/kg) given intravenously, and the variations in the resistance to inflation were recorded.

Blood samples were collected prior to and 1, 5 and 10 minutes following to PAF-challenge. Forty $\mu$l of blood were diluted in 10 ml isoton (Coultronics, France); erythrocytes were lysed with Zapoglobin (France) prior leukocytes were counted in a coulter counter. To determine platelet number, 40 $\mu$l of blood were diluted in 2 ml isoton and centrifuged at 100 runs per minute for 30 secondes, 100 $\mu$l of the supernatant were collected and further diluted in 10 ml isoton prior counting in a coulter counter.

TABLE NO. 1

Effects of 2-heptadecyl 2-methyl 4-[6'-(N-pyridinium) hexanoyloxymethyl] 1,3 dioxolan bromide on PAF-induced bronchoconstriction.

| | Doses mg/kg IV | n | Percentage Bronchoconstriction | Percentage Variation |
|---|---|---|---|---|
| Control | — | 8 | 79.8 +/− 3.22 | — |
| Compound | 5 | 3 | 3.5 +/− 1.53 | −95.6*** |
| of | 1 | 4 | 19.1 +/− 10.51 | −76.1*** |
| example | 0.5 | 6 | 23.6 +/− 7.15 | −70.4*** |
| No. 9 | 0.1 | 6 | 43.8 +/− 14.77 | −45.1** |

TABLE NO. 1-continued

Effects of 2-heptadecyl 2-methyl 4-[6'-(N-pyridinium) hexanoyloxymethyl] 1,3 dioxolan bromide on PAF-induced bronchoconstriction.

| Doses mg/kg IV | n | Percentage Bronchoconstriction | Percentage Variation |
|---|---|---|---|
| 0.05 | 3 | 79.0 +/− 9.27 | −1.0 NS |

LEGEND OF ALL THE TABLES:
NS Non Significative
*p < 0.05
**p < 0.01
***p < 0.001

TABLE NO. 2

Effects of 2-heptadecyl 2-methyl 4-[6'-(N-pyridinium) hexanoyloxymethyl] 1,3 dioxolan bromide on PAF-induced leukopenia.

| | Doses mg/kg IV | n | Time (mn) | Percentage Decrease of leukocyte number | Percentage Variation |
|---|---|---|---|---|---|
| Control | — | 8 | 1 | 40.8 +/− 7.18 | — |
| | | 8 | 5 | 29.2 +/− 10.89 | — |
| | | 8 | 10 | 33.5 +/− 5.04 | — |
| Compound | 5 | 3 | 1 | 16.5 +/− 2.42 | −59.6* |
| of | | 3 | 5 | 15.9 +/− 0.99 | −45.5 NS |
| example | | 3 | 10 | 18.7 +/− 5.08 | −44.2 NS |
| No. 9 | 1 | 4 | 1 | 3.5 +/− 12.60 | −91.4** |
| | | 4 | 5 | 2.9 +/− 10.51 | −90.1* |
| | | 4 | 10 | 1.0 +/− 22.62 | −97.0** |
| | 0.5 | 6 | 1 | 34.6 +/− 6.35 | −15.2 NS |
| | | 6 | 5 | 19.0 +/− 6.42 | −34.9 NS |
| | | 6 | 10 | 14.6 +/− 5.36 | −56.4 NS |
| | 0.1 | 6 | 1 | 41.8 +/− 6.50 | +2.5 NS |
| | | 6 | 5 | 31.9 +/− 4.88 | −9.2 NS |
| | | 6 | 10 | 33.5 +/− 4.65 | 0.0 NS |
| | 0.05 | 3 | 1 | 45.3 +/− 5.70 | +11.0 NS |
| | | 3 | 5 | 21.6 +/− 3.42 | −26.0 NS |
| | | 3 | 10 | 14.2 +/− 17.30 | −57.6 NS |

TABLE NO. 3

Effects of 2-heptadecyl 2-methyl 4-[6'-(N-pyridinium) hexanoyloxymethyl] 1,3 dioxolan bromide on PAF-induced thrombocytopenia

| | Doses mg/kg IV | n | Time (mn) | Percentage Decrease in leukocyte number | Percentage Variation |
|---|---|---|---|---|---|
| Control | — | 8 | 1 | 68.6 +/− 6.79 | — |
| | | 8 | 5 | 42.4 +/− 2.71 | — |
| | | 8 | 10 | 42.5 +/− 3.14 | — |
| Compound | 5 | 3 | 1 | 4.2 +/− 2.35 | −93.9*** |
| of | | 3 | 5 | 5.6 +/− 1.84 | −86.8*** |
| example | | 3 | 10 | 1.1 +/− 1.15 | −97.4*** |
| No. 9 | 1 | 4 | 1 | 11.5 +/− 6.21 | −83.2*** |
| | | 4 | 5 | 22.5 +/− 3.27 | −46.9* |
| | | 4 | 10 | 21.0 +/− 3.87 | −50.6* |
| | 0.5 | 6 | 1 | 19.3 +/− 10.19 | −71.9*** |
| | | 6 | 5 | 9.6 +/− 12.15 | −77.4*** |
| | | 6 | 10 | 10.9 +/− 9.94 | −74.4*** |
| | 0.1 | 6 | 1 | 30.1 +/− 13.72 | −56.1** |
| | | 6 | 5 | 34.7 +/− 3.60 | −18.2 NS |
| | | 6 | 10 | 42.3 +/− 4.79 | −0.5 NS |
| | 0.05 | 3 | 1 | 45.2 +/− 1.20 | −34.1 NS |
| | | 3 | 5 | 43.0 +/− 4.80 | +1.4 NS |
| | | 3 | 10 | 36.1 +/− 2.41 | −15.1 NS |

TABLE NO. 4

Effects of 2-heptadecyl 2-methyl 4-[6'-(N-quinolinium) hexanoyloxymethyl] 1,3 dioxolan bromide on PAF-induced bronchoconstriction.

| | Doses mg/kg IV | n | Percentage Bronchoconstriction | Percentage Variation |
|---|---|---|---|---|
| Control | — | 6 | 90.8 +/− 0.95 | — |
| Compound of | 1 | 5 | 8.1 +/− 2.91 | −91.1*** |
| Example | 0.5 | 5 | 25.1 +/− 6.53 | −72.4*** |
| No. 10 | 0.1 | 5 | 80.4 +/− 13.78 | −11.5 NS |

TABLE NO. 5

Effects of 2-heptadecyl 2-methyl 4-[6'-(N-quinolinium) hexanoyloxymethyl] 1,3 dioxolan bromide on PAF-induced leukopenia

| | Doses mg/kg IV | n | Time (mn) | Percentage Decrease in leukocyte number | Percentage Variation |
|---|---|---|---|---|---|
| Control | — | 6 | 1 | 41.4 +/− 8.0 | — |
| | | 6 | 5 | 28.7 +/− 6.9 | |
| | | 6 | 10 | 26.9 +/− 10.1 | |
| Compound of example No. 10 | 1 | 5 | 1 | 24.1 +/− 6.8 | −41.0 NS |
| | | 5 | 5 | 9.3 +/− 9.4 | −67.6** |
| | | 5 | 10 | 8.9 +/− 13.2 | −66.9** |
| | 0.5 | 5 | 1 | 17.0 +/− 12.9 | −58.9* |
| | | 5 | 5 | 9.0 +/− 11.8 | −68.6** |
| | | 5 | 10 | −7.6 +/− 17.5 | +128.3 NS |
| | 0.1 | 5 | 1 | 38.8 +/− 6.3 | +6.3 NS |
| | | 5 | 5 | 38.9 +/− 5.7 | +35.5 NS |
| | | 5 | 10 | 41.2 +/− 6.5 | +53.2 NS |

TABLE NO. 6

Effects of 2-heptadecyl 2-methyl 4-[6'-(N-quinolinium) hexanoyloxymethyl] 1,3 dioxolan bromide on PAF-induced thrombocytopenia

| | Doses mg/kg IV | n | Time (mn) | Percentage Decrease in leukocyte number | Percentage Variation |
|---|---|---|---|---|---|
| Control | — | 6 | 1 | 65.3 +/− 8.5 | — |
| | | 6 | 5 | 49.1 +/− 4.8 | |
| | | 6 | 10 | 48.5 +/− 0.5 | |
| Compound of example No. 10 | 1 | 5 | 1 | 19.3 +/− 1.4 | −58.3*** |
| | | 5 | 5 | 22.1 +/− 2.5 | −55.0** |
| | | 5 | 10 | 19.4 +/− 3.6 | −60.0** |
| | 0.5 | 5 | 1 | 26.2 +/− 6.3 | −59.9** |
| | | 5 | 5 | 29.8 +/− 1.7 | −39.3* |
| | | 5 | 10 | 32.1 +/− 5.8 | −33.8* |
| | 0.1 | 5 | 1 | 51.1 +/− 12.1 | −21.7 NS |
| | | 5 | 5 | 49.1 +/− 8.8 | 0 NS |
| | | 5 | 10 | 45.0 +/− 9.7 | −7.2 NS |

RESULTS 2-heptadecyl 2-methyl 4-[6'-(N-pyridinium) hexanoyloxymethyl] 1,3 dioxolan bromide (0 5, 1 and 5 mg/kg IV) and 2-heptadecyl 2-methyl 4-[6'-(N-quinolinium) hexanoyloxymethyl] 1,3 dioxolan bromide (0.5 and 1 mg/kg IV) inhibit the PAF-induced bronchoconstriction and the PAF-induced thrombocytopenia in the guinea-pig.

4—ANTIGEN-INDUCED BRONCHOCONSTRICTION, LEUKOPENIA AND THROMBOCYTOPENIA IN GUINEA-PIGS PASSIVELY SENSITIZED WITH HETEROLOGOUS SERUM

Intravenous injection of ovalbumin to guinea-pigs passively sensitized with rabbit anti-ovalbumin antiserum induces a bronchoconstriction associated with a leukopenia and a thrombocytopenia. This anaphylactic reaction appears to be due to the release of histamine and the generation of arachidonic acid metabolites (prostaglandins, thromboxane $A_2$ and leukotrienes). In the guinea-pig, the release of these autacoids is primarily mediated via immunoglobulins of the IgG class.

METHOD

Animals:
Hartley male guinea-pigs, Charles River (450–550 g).
Immunisation procedure:
Intravenous injection 18 h prior to challenge with the antigen of 0.5 ml/kg of ½ dilution of rabbit anti-ovalbumin antiserum.
Challenge is obtained by:
Ovalbumin, 0.75 mg/kg,
Intravenous injection of the antigen in a final volume of 1 ml/kg,
Vehicle, 0.15 M NaCl.
Compounds are administered by oral route in a volume of 2.5 ml/kg, 1 h prior to challenge with the antigen. After anesthesia by intraperitoneal injection of ethyl carbamate (1.5 g/kg) in a volume of 10 ml/kg.
Parameters monitored and expression of the data:
a—Bronchoconstriction
Antigen-induced bronchoconstriction in mm (A),
Maximal bronchoconstriction in mm (B).
The percentage of bronchoconstriction is calculated as follows:

$$\frac{A \times 100}{B}$$

Neutrophil and platelet counts were performed 1 minute prior to and 1,5 and 10 minutes after challenge. The changes were expressed in percentages calculated over the values obtained one minute prior to challenge.
The following equipement was used:
Ugo Basile, Comerio ITALY,
Rodent ventilator ref. 7025
Bronchospam transducer ref. 7020
Two-Channel Recorder "GEMINI" ref. 7070
Coultronics, FRANCE
Coulters Counter Z B I

TABLE NO. 7

Effects of 2-heptadecyl 2-methyl 4-[6'-(N-pyridinium) hexanoyloxymethyl] 1,3 dioxolan bromide on antigen-induced bronchoconstriction

| | Dose mg/kg IV | n | Percentage Bronchoconstriction | Percentage Variation |
|---|---|---|---|---|
| Control | — | 6 | 71.9 +/− 14.2 | — |
| Compound of example No. 9 | 5 | 8 | 51.3 +/− 14.2 | −28.7 NS |

TABLE NO. 8

Effects of 2-heptadecyl 2-methyl 4-[6'-(N-pyridinium) hexanoyloxymethyl] 1,3 dioxolan bromide on antigen-induced leukopenia

| | Dose mg/kg IV | n | Time (mn) | Percentage Decrease in leukocytes number | Percentage Inhibition |
|---|---|---|---|---|---|
| Control | — | 6 | 1 | −11.8 +/− 5.1 | — |
| | | 6 | 5 | −39.6 +/− 9.5 | |
| | | 6 | 10 | −53.9 +/− 7.1 | |
| Compound of example No. 9 | 5 | 8 | 1 | −15.6 +/− 6.6 | +32.0 NS |
| | | 8 | 5 | −8.7 +/− 10.7 | −78.0* |
| | | 8 | 10 | −12.3 +/− 14.1 | −77.2* |

TABLE NO. 9

Effects of 2-heptadecyl 2-methyl 4-[6'-(N-pyridinium) hexanoyloxymethyl] 1,3 dioxolan bromide on antigen-induced thrombocytopenia

| | Dose mg/kg IV | n | Time (mn) | Percentage Decrease in leukocytes number | Percentage Inhibition |
|---|---|---|---|---|---|
| Control | — | 6 | 1 | −6.8 +/− 2.7 | — |
| | | 6 | 5 | −39.7 +/− 12.5 | |
| | | 6 | 10 | −26.1 +/− 8.1 | |
| Compound of example No. 9 | 5 | 8 | 1 | +0.3 +/− 7.9 | −104.4 NS |
| | | 8 | 5 | −3.5 +/− 3.1 | −91.2** |
| | | 8 | 10 | −15.7 +/− 6.2 | −39.8 NS |

RESULTS 2-heptadecyl 2-methyl 4-[6'-(N-pyridinium) hexanoyloxymethyl] 1,3 dioxolan bromide (5 mg/kg IV) antagonizes antigen-induced leukopenia and thrombocytopenia without significantly reducing antigen-induced bronchoconstriction.

5—ACTION OF PAF-INDUCED HYPOTENSION IN THE ANESTHETIZED RAT

MATERIALS AND METHOD:

Male Sprague Dawley Rats (Charles River Breeding Station) (250-300 g) were anesthetized with ethyl carbamate at the dose of 1.2 g/kg IP.

Intravenous injection of PAF provokes a dose-dependent hypotension. The effects of 2-heptadecyl 2-methyl 4-[6'-(N-pyridinium) hexanoyloxymethyl] 1,3 dioxolan bromide and 2-heptadecyl 2-methyl 4-[6'-(N-quinolinium, hexanoyloxymethyl] 1,3 dioxolan bromide were sought against PAF-induced hypotension, in curative treatments. Hypotension was provoked by 1 single dose of PAF (1 µg/kg) in an intravenous injection, directly into the penis vein, in a volume of 0.1 ml/100 g. At the maximum hypotension, i.e. 3 minutes after PAF injection, drugs were administered.

Parameters measured and expression of the results:

The systolic and diastolic arteial pressures (mmHg) were measured. The values were expressed as mean +/− SEM in the accompanying figures wherein.

Figure 1:
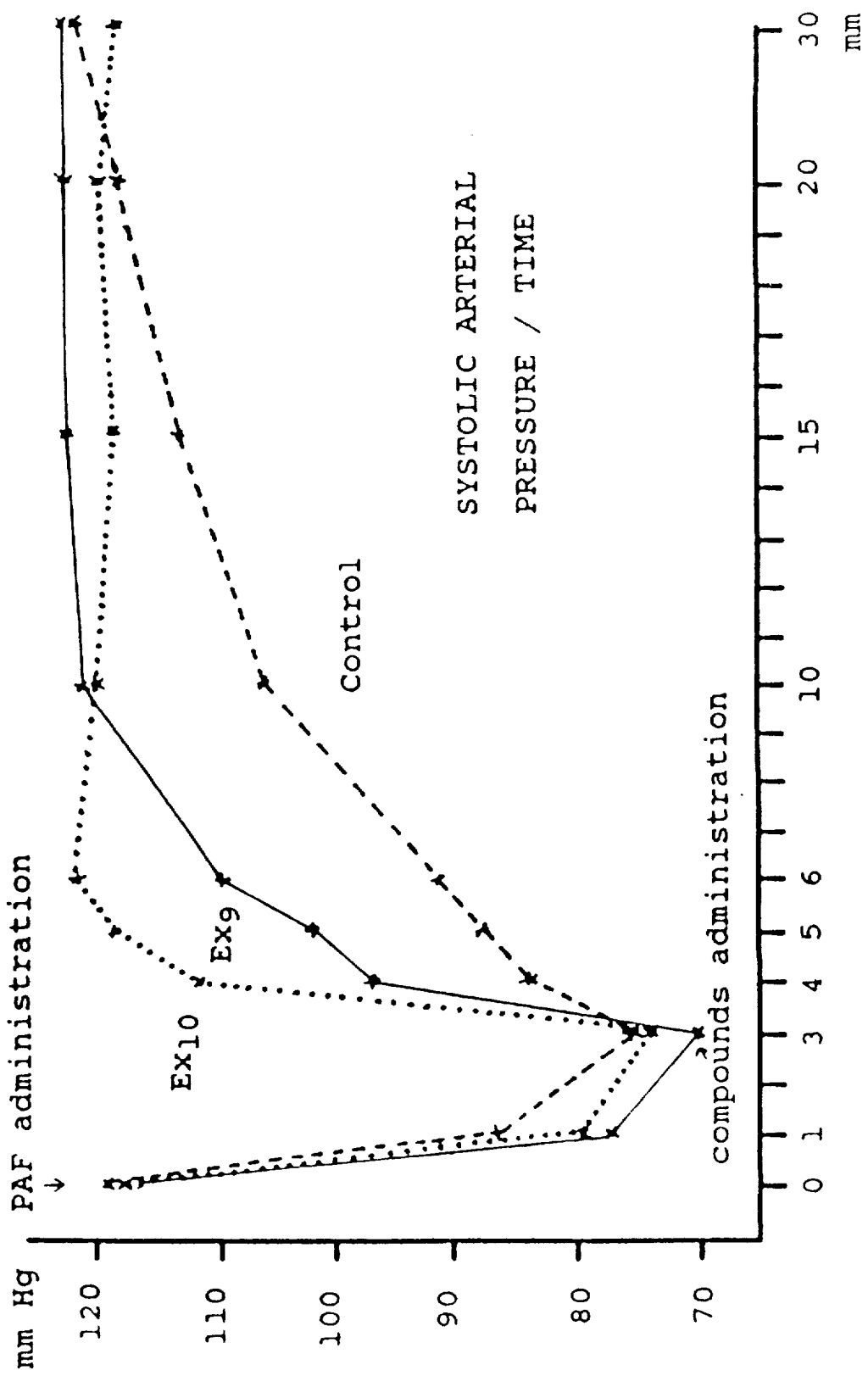
FIG. 1 is a graph of systolic arterial pressure vs. time.

Measurement apparatus:

Gould $P_{50}$ transducer to measure arterial pressure,
Braun perfuser,
Gould 8000 S polygraphic recorder.

6—ANTAGONISM OF THE POLYMORPHONUCLEAR LEUKOCYTE AGGREGATION INDUCED BY PAF

Polymorphonuclear leukocytes (PMNs) were obtained as described by A. W. Ford-Hutchinson et al. (Br - J. Pharmacol. 76, 367–371, 1982). Cell suspensions (<90% PMNs) were prepared from peritoneal exudates obtained after a 5 ml IP injection of sodium caseinate 12% (w/v) to male Wistar rats, 300 g body weight.

After centrifugation, cells were washed with Hanks and resuspended in MEM/Hepes 30 mM medium (PM=7.4) at a concentration of $10^7$ cells/ml. Cytochalasin B (5 µg/ml) was added 10 minutes before triggering aggregation to amplify the PMNs aggregation. The light transmittance through the cell suspension (400 µl) was measured under a 900 R/mn magnetic stirring, with a dual beam aggregometer (Chronolog Corp. Coultronics.)

The control cuvet is the cell suspension diluted to 20% of the cell count with MEM and the difference represents 100% transmittance. Change in transmittance, which occurs when PAF is added, was continuously recorded.

Drugs solubilized in MEM/Hepes were added (4 µl) to PMNs suspension 2 minutes before PAF addition.

RESULTS

PAF $10^{-8}$ induced 55 to 70% aggregation of this PMNs suspension.

2-heptadecyl 2-methyl 4-[6'-(N-pyridinium hexanoyloxymethyl] 1,3 dioxolan bromide and 2-heptadecyl 2-methyl 4[6'-(N-quinolinium) hexanoyloxymethyl] 1,3 dioxolan bromide dose-dependently inhibit this aggregation with respective $IC_{50s}$:

2-heptadecyl 2-methyl 4-[6'-(N-pyridinium) hexanoyloxymethyl] 1,3 dioxolan bromide: $5 \times 10^{-7}$ M.

2-heptadecyl 2-methyl 4-[6'-(N-quinolinium) hexanoyloxymethyl] 1,3 dioxolan bromide: $10^{-6}$ M.

7—INHIBITION OF INTRACYTOSOLIC FREE CALCIUM MOBILIZATION INDUCED BY PAF IN WASHED RABBITS PLATELETS

Blood was taken from the auricular artery of the rabbit on citric acid/sodium citrate/dextrose and anticoagulan and the washed platelets were prepared according to Ardlie et al., Brit. J. Pharmacology, 19, 7–17, 1970. They were incubated with acetylsalicylic salt (100 µM, 30 minutes) to avoid thromboxane induced aggregation. They were then loaded with the fluorescent calcium indicator dye quin 2 by incubation with quin 2 aceto-methylester (15 µM in DMSO, 20 minutes at room temperature) which penetrates the cell membrane and after hydrolysed is trapped in the platelet. Drugs were preincubated with platelets for 15 minutes simultaneously to CP/CPK mixture which destroys secreted ADP.

Fluorescent measurement was then performed (excitation λ=339 nm, emission λ=494 nm) after PAF addition to platelet suspension. The fluorescence intensity is proportional to the cytosolic free calcium level $[Ca^{2+}]i$ which can be quantified as described by Tsien et al., J. Cell Biol., 94, 325–334, 1982.

RESULTS

Platelet stimulation induced by PAF $2 \times 10^{-9}$M increased the [$Ca^{2+}$]i level from about 150 nM at resting state to 400–600 nM.

2-heptadecyl 2-methyl 4-[6'-(N-pyridinium) hexanoyloxymethyl] 1,3 dioxolan bromide and 2-heptadecyl 2-methy 4-[6'-(N-quinolinium) hexanoyloxymethyl] 1,3 dioxolan bromide at $5 \times 10^{-7}$M totally inhibit the PAF-induced [$Ca^{2+}$]i mobilization. At $5 \times 10^{-8}$M, the inhibition of PAF effect is respectively 44% for 2-heptadecyl 2-methyl 4-[6'-(N-pyridinium hexanoyloxymethyl] 1,3 dioxolan bromide and 75% for 2-heptadecyl 2-methyl 4-[6'-(N-quinolinium) hexanoyloxymethyl] 1,3 dioxolan bromide.

POSOLOGY

In human therapy, by oral administration, daily doses are from 0.1 to 0.5 mg in tablets or capsules with an enteric coating; by IV route, the corresponding daily doses are from 0.01 to 0.05 mg. Treatment is generally from 2 to 6 weeks.

We claim:

1. Aminoacylates of glycerol acetal of the formula I

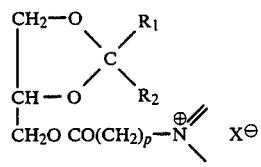

wherein
R$_1$ represents trimethoxy phenyl or a straight or branched chain alkyl group of the formula $C_mH_{2m+1}$, m being an integer of from 9 to 25, R$_2$ represents a hydrogen atom, a phenyl group or a group of the formula $C_nH_{2n+1}$, n being an integer of from 1 to 10, p is an integer of from 3 to 10,

represents pyridinium and $X^\ominus$ means the anion of a pharmaceutically acceptable inorganic or organic acid.

2. The aminoacylates of glycerol acetal of claim 1 wherein $X^\ominus$ is the anion of chlorine, bromine, iodine, benzoic acid, acetic acid, methane sulfonic acid, or tartaric acid.

3. An aminoacylate of glycerol acetal of claim 1 and 2 in the form of a mixture of the cis and trans isomers.

4. An aminoacylate of glycerol acetal of claim 1 and 2 in the form of the trans isomer.

5. An aminoacylate of glycerol acetal of claim 1 and 2 in the form of the cis isomer.

6. An anti-PAF therapeutic composition of matter containing as an active ingredient therein one or more of the compounds according to claim 1 and 2 associated with a pharmaceutically acceptable diluent or carrier, the total amount of compound according to claim 1 and 2 being an amount sufficient to be effective as an anti-PAF agent.

* * * * *

UNITED STATES PATENT AND TRADEMARK OFFICE
CERTIFICATE OF CORRECTION

PATENT NO. : 4,921,865

DATED : May 1, 1990

INVENTOR(S) : Colette Broquet et al.   Page 1 of 5

It is certified that error appears in the above-identified patent and that said Letters Patent is hereby corrected as shown below:

Front page of the patent, in the Abstract, line 10, change "a integer" to --an integer--.

Column 2, line 15, delete the formula and substitute therefor the following:

Column 3, lines 5-10, delete the formula and substitute therefor the following:

$R_1 = C_{17}H_{35}$ , $R_2 = CH_3$ , $-\overset{\oplus}{N}\diagup\hspace{-0.5em}\diagdown)$ = pyridinyl, x = Cl, p = 3.

Column 3, line 40, change "4-(4'-chlorobutylryloxymethyl)" to --4-(4'-chlorobutyryloxymethyl)--.

Column 5, line 18, change "1,3-dixolan" to --1,3-dioxolan--; cancel lines 35-60 and substitute therefor the following:

$R_1 = C_{17}H_{35}$ , $R_2 = H$ , $-\overset{\oplus}{N}\diagup\hspace{-0.5em}\diagdown)$ = pyridinyl , x = Cl, p = 3.

<u>2</u> b    rf : 0.17 (petroleum ether / diethyl ether 30:70 by volume)

<u>3</u> b    rf : 0.37 (petroleum ether / diethyl ether 70:30 by volume)

$I_b$    rf : 0.16 (chloroform / methanol 70:30 by volume)

$I_b$ NMR instead of $CH_3$ at 1.4 ($-O\diagdown\hspace{-0.6em}\diagup^{-O}CH_3$)

2 multiplets centered on 4.9 ppm ($-O\diagdown\hspace{-0.6em}\diagup^{-O}H$)

UNITED STATES PATENT AND TRADEMARK OFFICE
CERTIFICATE OF CORRECTION

PATENT NO. : 4,921,865
DATED : May 1, 1990
INVENTOR(S) : Colette Broquet et al.

It is certified that error appears in the above-identified patent and that said Letters Patent is hereby corrected as shown below:

Column 5, line 66, change "dioxalan" to --dioxolan--.

Column 6, line 28, add the following:
--$I_C$ NMR instead of $CH_3$ at 1.4--

Column 9, line 33, change "MEOH" to --MeOH--.

Column 10, line 39, change "25 g" to --2.5 g--.

Column 13, line 55, change "05" to --0.5--.

Column 15, line 59, change "arteial" to --arterial--.

Column 16, line 36, change "4[6'-(N-quinolinium" to --4-[6'(N-quinolinium--.

Column 17, lines 27-32, delete the formula and substitute therefor the following:

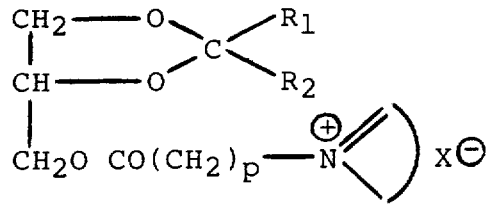

UNITED STATES PATENT AND TRADEMARK OFFICE
CERTIFICATE OF CORRECTION

PATENT NO. : 4,921,865

DATED : May 1, 1990

INVENTOR(S) : Colette Broquet et al.     Page 3 of 5

Figure 2:
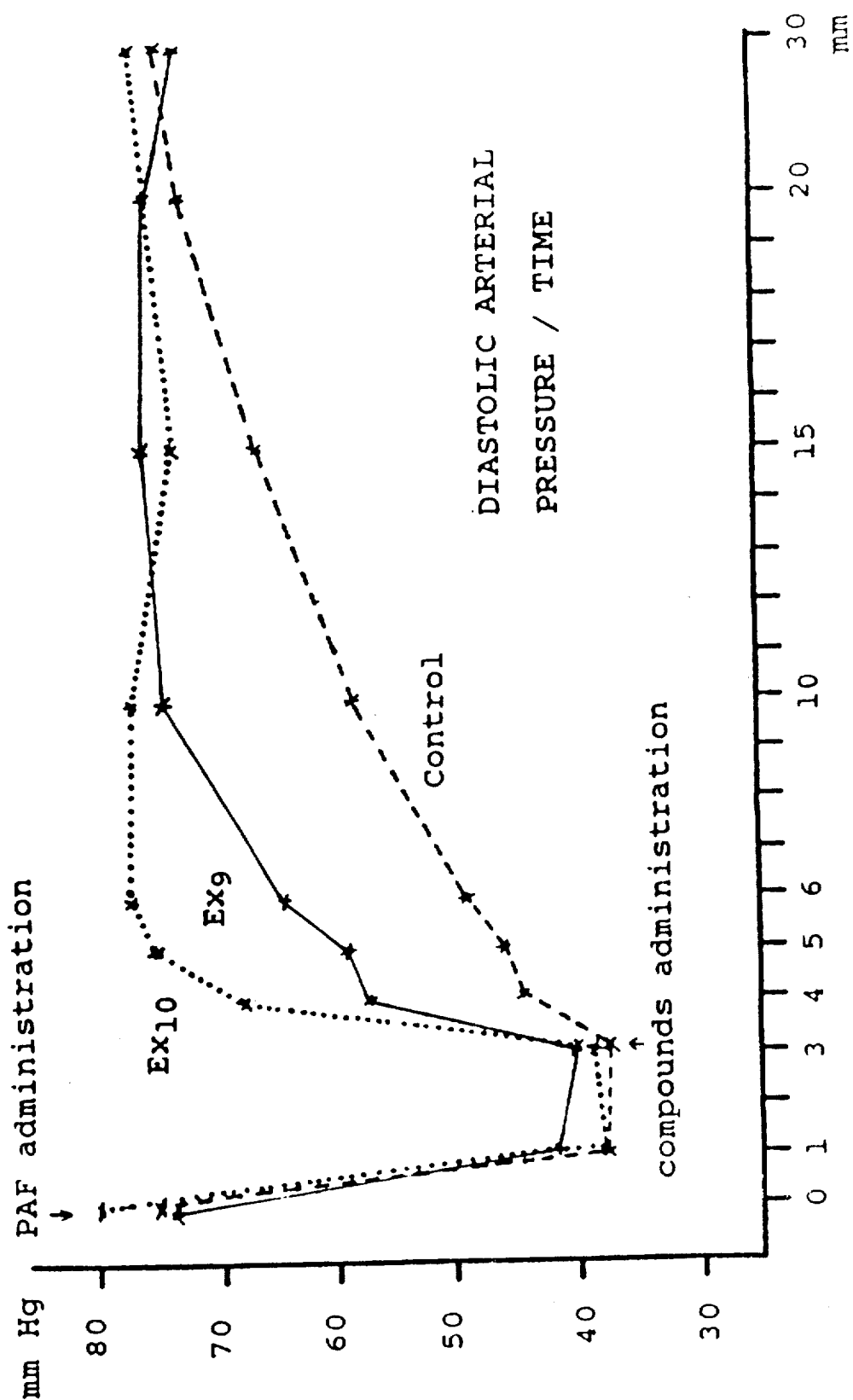
FIG. 2 is a graph of diastolic arterial pressure vs. time.

It is certified that error appears in the above-identified patent and that said Letters Patent is hereby corrected as shown below:

Insert drawing Figures 1 and 2 as shown on attached sheets.

Signed and Sealed this

Twenty-ninth Day of January, 1991

*Attest:*

HARRY F. MANBECK, JR.

*Attesting Officer*     *Commissioner of Patents and Trademarks*